(12) United States Patent
Jansen et al.

(10) Patent No.: US 8,211,027 B2
(45) Date of Patent: Jul. 3, 2012

(54) METHOD AND APPARATUS FOR DETERMINING AT LEAST ONE PATIENT-RELATED PARAMETER FOR MONITORING A PATIENT

(75) Inventors: Jozef Reinier Cornelis Jansen, Noordwijkerhout (NL); Johannes Jacobus Schreuder, Verese (IT)

(73) Assignees: Jozef R. C. Jansen, Noordwijkerhout (NL); Johannes J. Schreuder, Varese (IT)

( * ) Notice: Subject to any disclaimer, the term of this patent is extended or adjusted under 35 U.S.C. 154(b) by 1197 days.

(21) Appl. No.: 11/914,655

(22) PCT Filed: Apr. 27, 2006

(86) PCT No.: PCT/EP2006/061869
§ 371 (c)(1),
(2), (4) Date: Nov. 16, 2007

(87) PCT Pub. No.: WO2006/122868
PCT Pub. Date: Nov. 23, 2006

(65) Prior Publication Data
US 2008/0208062 A1    Aug. 28, 2008

(30) Foreign Application Priority Data
May 19, 2005   (EP) .................................... 05104234

(51) Int. Cl.
*A61B 5/02*    (2006.01)
(52) U.S. Cl. ......... 600/481; 600/485; 600/486; 600/526
(58) Field of Classification Search .................. 600/301, 600/481–507, 526
See application file for complete search history.

(56) References Cited

U.S. PATENT DOCUMENTS

| | | | |
|---|---|---|---|
| 3,841,313 A | 10/1974 | Wesseling et al. | |
| 4,595,015 A | 6/1986 | Jansen | |
| 5,183,051 A | 2/1993 | Kraidin | |
| 5,400,793 A * | 3/1995 | Wesseling | 600/485 |
| 5,450,850 A | 9/1995 | Iinuma et al. | |
| 6,348,038 B1 | 2/2002 | Band | |
| 2002/0022785 A1 | 2/2002 | Romano | |
| 2004/0024324 A1 | 2/2004 | Bratteli | |
| 2004/0167413 A1 | 8/2004 | Brattell | |
| 2006/0235323 A1 * | 10/2006 | Hatib et al. | 600/526 |

FOREIGN PATENT DOCUMENTS
EP    1154720    2/2000
(Continued)

OTHER PUBLICATIONS de Vaal et al., "Less invasive determination of cardiac output from the arterial pressure by aortic diameter-calibrated pulse contour", Br J Anaesth, (2005), 95 (3), 326-31.*

(Continued)

*Primary Examiner* — Miranda Le
*Assistant Examiner* — Michael Catina
(74) *Attorney, Agent, or Firm* — Steven M. Koehler; Westman, Champlin & Kelly, P.A.

(57) ABSTRACT

A method is described for determining at least one patient-related parameter for monitoring a patient. A general population-related non-linear pressure/CSA relationship of the arterial vascular bed is used and the arterial pressure of the patient is measured to obtain a prediction of the cross sectional area (CSA) of the thoracic part of the aorta. The cross sectional area is measured, wherein at least one parameter of the general population-related non-linear pressure/CSA relationship is corrected by means of the measured cross sectional area to determine a patient-related non-linear pressure/CSA relationship such that the cross sectional area obtained with this patient-related pressure/CSA relationship is equal to the measured cross sectional area.

15 Claims, 7 Drawing Sheets

FOREIGN PATENT DOCUMENTS

| | | |
|---|---|---|
| WO | WO 9724690 | 7/1997 |
| WO | WO 00/53087 | 9/2000 |

OTHER PUBLICATIONS

Official Search Report of the European Patent Office in counterpart foreign application No. 05104234.9 filed May 19, 2005.
Written Opinion of the European Patent Office in counterpart foreign application No. 05104234.9 filed May 19, 2005.

Kortnet et al. J Physiol. (1998) 512: 917-926.
Boulnois et al J Clin Monit (2000) 16:127-140.
Murgo and Westerhof Circ Res (1984) 54: 666-673.
Remington et al., "Volume elasticity characteristics of the human aorta and prediction of the stroke volume from the pressure pulse", Am. J. Physiol (1948) 153: 298-308.
Langewouters et al., Journal of Biomechanics (1984), 17, 425-435.

* cited by examiner

METHOD AND APPARATUS FOR DETERMINING AT LEAST ONE PATIENT-RELATED PARAMETER FOR MONITORING A PATIENT

CROSS-REFERENCE TO RELATED APPLICATION

This application is a Section 371 National Stage Application of International Application No. PCT/EP2006/061869, filed Apr. 27, 2006 and published as WO 2006/122868 A1 on Nov. 23, 2006, in English.

BACKGROUND

The discussion below is merely provided for general background information and is not intended to be used as an aid in determining the scope of the claimed subject matter. A method and apparatus for determining at least one patient-related parameter for monitoring a patient, comprising using a general population-related non-linear pressure/CSA relationship of the arterial vascular bed and measuring the arterial pressure of the patient to obtain a prediction of the cross sectional area (CSA) of the thoracic part of the aorta, and to a method and apparatus for determining at least one patient-related parameter for monitoring a patient, comprising using a general population-related non-linear CSA/pressure relationship of the arterial vascular bed and measuring the CSA to obtain a prediction of the arterial pressure.

In U.S. Pat. No. 3,841,313 it has been suggested that the systolic area could be used to determine stroke volume. The systolic area is the area between the blood pressure and end diastolic pressure during systole. There have been published many modifications of this so-called pulse contour technique, see for instance U.S. Pat. No. 5,183,051. One of the major shortcomings of these pulse contour methods is their reliance upon measuring morphological features of the blood pressure waveform. In particular, the position of the upstroke and the position of the dicrotic notch, which positions indicate the opening and closing of the aortic valve respectively, must be found in order to measure the systolic area. In patients the dicrotic notch appears difficult to detect. WO 9724690 discloses an apparatus which determines the opening and closing time of the aortic valve by means of a three element windkessel model of the circulation. Said apparatus also functions in those cases where the heartbeat is irregular.

U.S. Pat. No. 5,400,793 describes another method for determining the stroke volume from aortic blood pressure in a human. The method comprises calculation of blood flow from aortic pressure and integration of the flow over the systolic period, the aorta being regarded as a transmission line supplemented with a windkessel compliance and the pressure/volume relationship in the aorta as an arctangent relationship. The characteristic of the transmission line and the windkessel compliance are continuously adapted to the pressure of the windkessel compliance for each stroke concerned. Additionally, to calculate the aortic flow to the windkessel, the flow through the peripheral resistance is added to the flow into the windkessel compliance.

According to Langewouters et al., J Biomechanics (1984) 17, 425-435, the relationship between the thoracic cross sectional area (CSA) of the aorta and the pressure in the aorta can be specified using the formula:

$$CSA(Pa) = CSA\max\left[0.5 + \frac{1}{\pi}\arctan\left(\frac{Pa - P_0}{P_1}\right)\right] \quad (1)$$

where CSA(Pa) is the thoracic cross sectional area as a function of the pressure Pa, CSAmax is the limit cross sectional area at very high pressure, and P0 and P1 are, respectively, the pressure at the point of inflection of the relationship and the slope of the relationship at the point of inflection. The slope is defined by the width between the points at one-half and three-quarter of CSAmax. The values of the parameters CSAmax, P0 and P1, are known from the work of Langewouters et al. In particular, these parameters depend on the sex and age of the person. In the prior art these parameters are used in monitoring applications, wherein the pulse contour model is used. However, the value for CSAmax has a dispersion of approximately 20%. Therefore, it is not possible to determine the values of the components in the pulse contour model in an absolute sense without more exact calibration, as a standard deviation of approximately 20% is regarded as unacceptable, in particular in patient monitoring applications.

U.S. Pat. No. 6,348,038 describes another method for measuring cardiac output using pulse contour analysis. A non-linear transformation is used to correct for the changing characteristics of the arterial system with pressure and autocorrelation is then used to derive the cardiac output. The method determines the nominal stroke volume from the modulus of the first harmonic from the arterial pressure and obtains nominal cardiac output and systemic vascular resistance. In this method, the pressure waveform obtained from a patient is transformed into a volume waveform, for instance via a 'look-up' table, with the mean of the data of the pressure-volume relationship of the arterial system based on a population average. The basic approximation to a look up table is known in the art.

A series of pressure-volume curves is described in Remington et al., "Volume elasticity characteristics of the human aorta and prediction of the stroke volume from the pressure pulse", Am. J. Physiol (1948) 153: 298-308. A used equation has the form of:

$$SV_N = \frac{P_{1H}}{HR\ \exp(-0.0092\ MAP)} \quad (2)$$

where $SV_N$ is nominal Stoke Volume, $P_{1H}$ is modulus of first harmonics of the arterial pressure, MAP is mean arterial blood pressure and HR is heart rate. The value 0.0092 is related to a population average.

Also, Kortnet et al. J. Physiol. (1998) 512: 917-926 describe the non-linear relationship between the cross sectional area and pressure of the aorta using the formula:

$$CSA(Pa) = A\min + \frac{A\max - A\min}{1 + \exp[(P_0 - Pa)/P_1]} \quad (3)$$

where, CSA(Pa) is the thoracic cross sectional area of the aorta as a function of the pressure Pa, Amin is the area at zero pressure (usually Amin=0), Amax is the area at very high pressure, P0 is the inflection point, and P1 is the slope of the relationship at the point of inflection. The values for the parameters of this relationship are known based on population averages.

Accurate cross sectional area (CSA) measurements of the aorta are known from Boulnois et al J Clin Monit (2000) 16:127-140. The described non-invasive transesophageal ultra-sound approach allows a continuous measurement over time of the CSA of the aorta, resulting in a patient-specific CSA determination.

It is now accepted in the art that all existing pulse contour methods require calibration for improved accuracy because the value of the parameters of the used pressure/volume or pressure/CSA relationships are based on population averaged values and are, thus, not necessarily valid for a specific individual patient.

A calibration, for example based on the thermodilution or indicator dilution method, as described in EP-A-1 154 720 is highly repeatable and only one single determination is required to give mean cardiac output. However, these thermodilution calibration methods require highly invasive techniques of placement of catheters into the blood stream of a patient.

SUMMARY

This Summary and Abstract are provided to introduce some concepts in a simplified form that are further described below in the Detailed Description. This Summary and Abstract are not intended to identify key features or essential features of the claimed subject matter, nor are they intended to be used as an aid in determining the scope of the claimed subject matter. In addition, the description herein provided and the claimed subject matter should not be interpreted as being directed to addressing any of the short-comings discussed in the Background.

A method is provided wherein the cross sectional area is measured, wherein at least one parameter of the general population-related non-linear pressure/CSA relationship is corrected by means of the measured cross sectional area to determine a patient-related non-linear pressure/CSA relationship, and wherein the cross sectional area obtained with this patient-related pressure/CSA relationship is equal to the measured cross sectional area. In this manner adaptation of a given population-related pressure/CSA or pressure/volume relationship into an individual patient-related pressure/CSA or pressure/volume relationship is provided by means of a comparison of the predicted CSA or volume obtained via the relationship with a measured CSA or volume, for instance measured by ultra sound.

According to a further embodiment of the invention this individual patient-related pressure/CSA relationship is used to construct an improved pulse contour method for measuring stroke volume and cardiac output.

According to an aspect the invention the method for determining at least one patient-related parameter for monitoring a patient, comprising using a general population-related non-linear CSA/pressure relationship of the arterial vascular bed and measuring the CSA to obtain a prediction of the arterial pressure is characterized in that the arterial pressure is measured, wherein at least one parameter of the general population-related non-linear CSA/pressure relationship is corrected by means of the measured arterial pressure to determine a patient-related non-linear CSA/pressure relationship, wherein the arterial pressure obtained with this patient-related relationship is equal to the measured arterial pressure. In this manner, this aspect of the invention allows a continuous monitoring of the arterial pressure from a continuous measurement of the diameter or CSA of the aorta.

BRIEF DESCRIPTION OF THE DRAWINGS

The invention will now be explained in more detail with reference to the drawings, which schematically shows an embodiment of the apparatus according to the invention.

The principles of the invention will first be described with reference to FIGS. 1-6.

DETAILED DESCRIPTION OF THE ILLUSTRATIVE EMBODIMENTS

Figure 1:
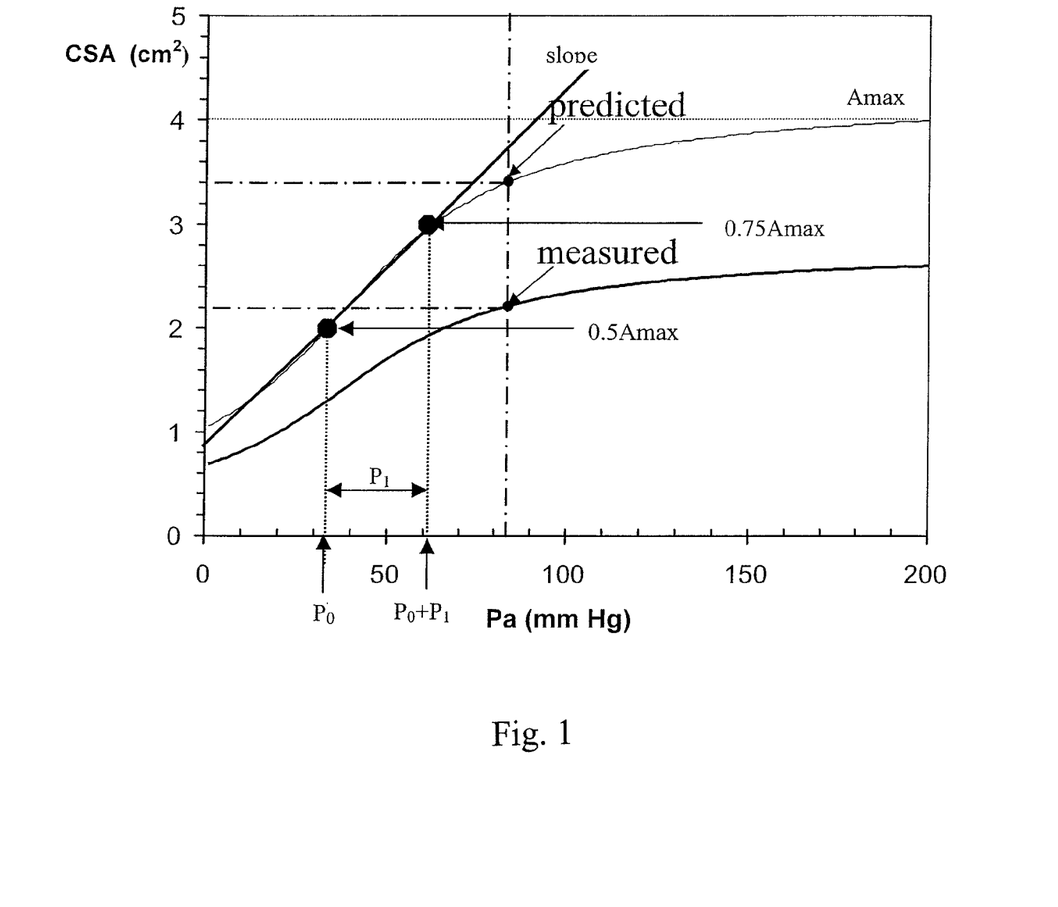
FIG. 1 shows an arctangent pressure/CSA relationship according to equation 1.

According to an aspect of the invention a population-related pressure/CSA relationship can be corrected to obtain an individual patient-related pressure/CSA relationship. It is known that the aortic Windkessel compliance (the first derivative—or slope—of the pressure/CSA relationship) decreases substantially when aortic pressure increases. FIG. 1 shows the arctangent pressure/CSA relationship according to equation (1), wherein this non-linear behaviour of the aortic wall can be seen. This non-linear behaviour would be a major source of error if not taken into account. As mentioned above, the non-linear relationships, in these examples, were studied in vitro by Langewouters et al. and described as mathematical functions whose properties regress tightly on a patient's age and gender, and depend slightly on patient height and weight, except for the maximal cross sectional area (CSAmax) of the aorta.

Figure 2:
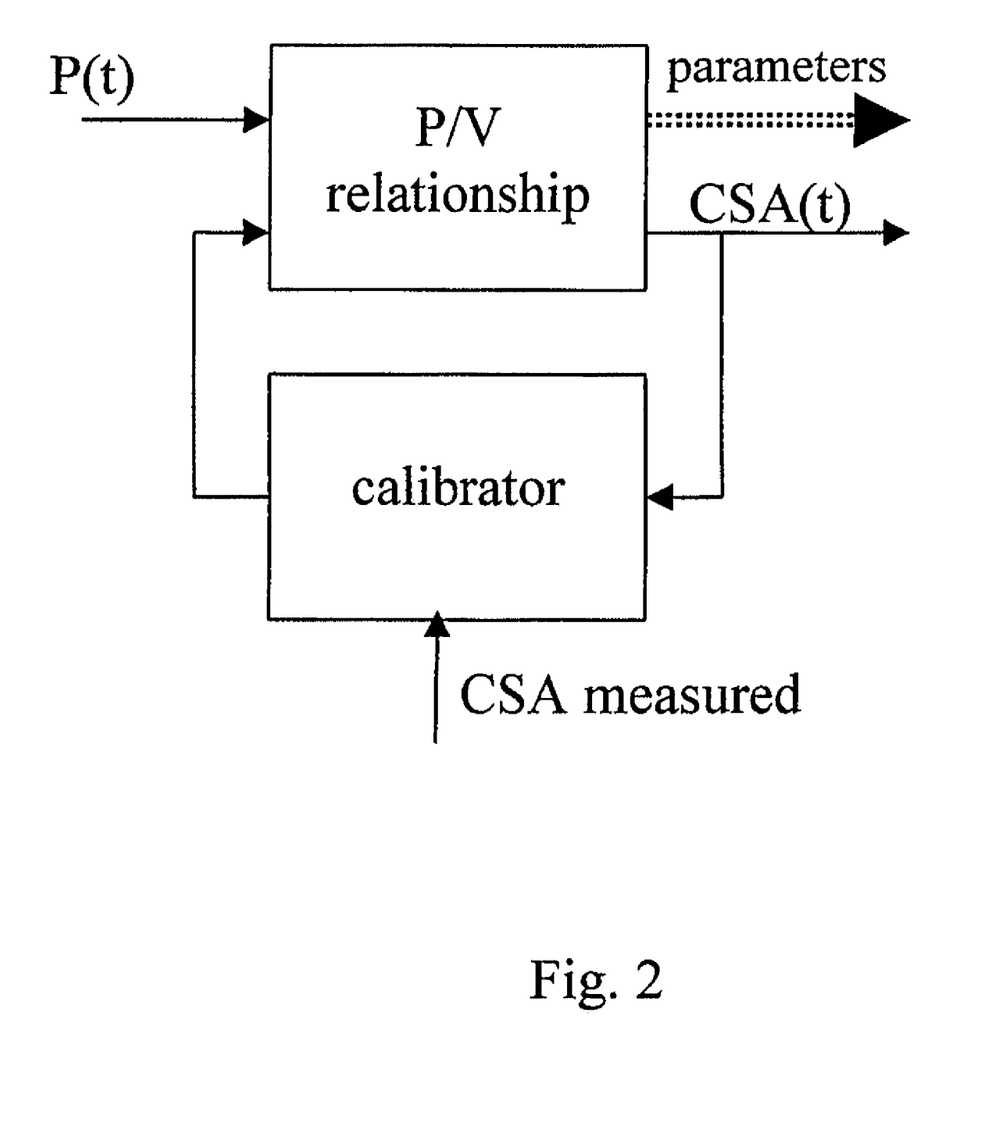
FIG. 2 schematically illustrates the prediction of the CSA of the aorta from a measure of the arterial pressure and the correction of the population-related pressure/CSA relationship into a patient-related pressure/CSA relationship by means of an independent measure of the actual CSA of the aorta of a patient.

According to an aspect of the invention the individual uncertainty in the aortic CSA in each patient is overcome by carrying out a real time measurement of aortic diameter, in this example with an ultra sound echo system (for instance M-mode, HemoSonic 100, Arrow International Inc.). CSA is measured at least once in an individual patient. Next, the population-related arctangent relationship between pressure and CSA (as shown FIG. 1) is linearly scaled by means of the measured CSA value as schematically shown in FIG. 2. This linear scaling results in a new value for CSAmax which is characteristic for the patient under study.

In FIG. 1 the result of this scaling step can be seen. In FIG. 1, $P_0$, $P_1$ and CSAmax are population-related parameters of the arctangent relationship. CSA is the thoracic cross sectional area of the aorta (CSA=diameter$^2$*π/4), and Pa is the arterial pressure. The predicted curve of a 59 year old female with a length of 160 cm and weight of 48 kg using the population-related parameters is shown as a thin solid line. The corrected patient-related relationship scaled from the predicted CSA curve (diameter 20.7 mm) using the measured CSA (diameter 16.7 mm) at a arterial pressure of 82 mmHg is shown as a thick solid line.

It is noted that a similar approach can be used for other known descriptions of pressure/CSA or pressure/volume relationships, such as the relationships according to equations (2) and (3). Therefore, in this description and in particular in the claims the wording CSA and measurement of CSA should be understood as to encompass any volume related or segmental volume related value and measurement thereof.

Figure 3:
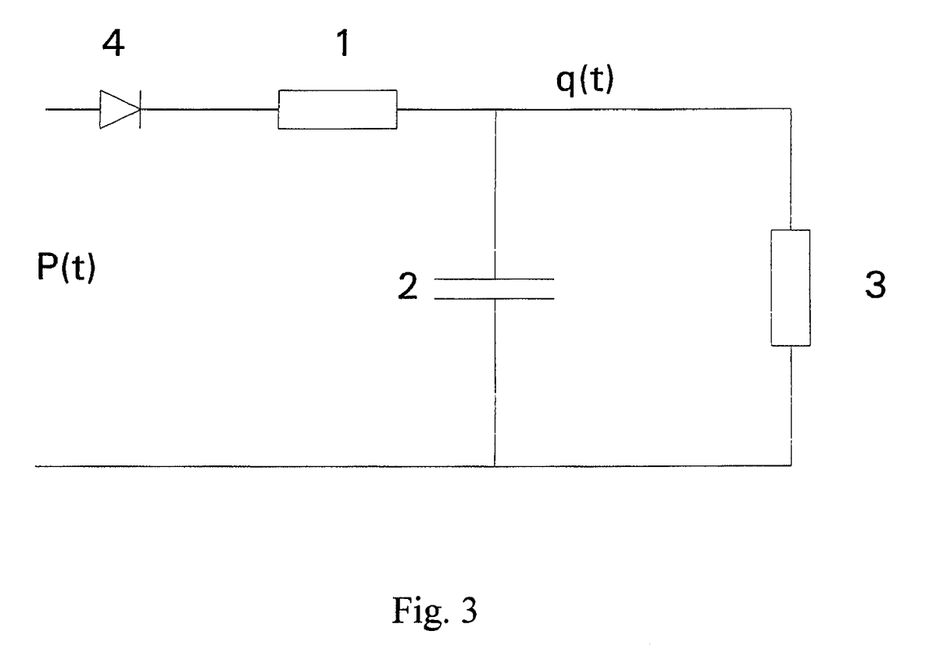
FIG. 3 shows an equivalent circuit diagram of the heart valve and the arterial vascular system, a so-called Windkessel model.

According to an aspect of the invention a pulse contour method is improved if the pulse contour method uses parameters obtained from the patient-specific pressure/CSA relationship. FIG. 3 shows a Windkessel model which is an equivalent circuit diagram of the heart valve and the arterial vascular system describing the load on the heart. The model comprises the following elements: a characteristic input resistance, Rao, 1; an arterial compliance, Cw, 2; a peripheral resistance, Rp, 3; and a heart valve, D, 4, which closes after the blood flow rate in the cardiac cycle becomes negative.

As Pa varies in time in a patient also the parameters Rao, and Cw of the model varies in time. Computation of the blood flow rated with time variant model parameters can be performed with complex model simulations. According to the invention two more simple solutions are possible.

In the first solution the values of Rao and Cw are calculated based on the patient-related pressure/CSA relationship for the mean value of Pa of the previous heart beats or of the mean Pa value of the heartbeat under analysis. The values of Rao and Cw are kept constant for the pressure values, Pa, during the heartbeat under analysis. The pressure, Pa, is applied to a linear pulse contour model as described below.

In the second solution, after calculating Rao and CW as described in solution 1, the pressure values within the heart beat are transformed with use of the patient-related pressure/CSA relationship in such a manner that each equal change of the pressure value results in an equal change of blood volume. After having found a mean pressure for a heartbeat of for instance 70 mmHg, for example a pressure value of 110 mmHg is converted with use of the patient-related pressure/CSA relationship to a pressure value of 95 mmHg. Similarly, for example a pressure value of 60 mmHg is converted to a pressure value of 62 mmHg. The resulting transformed pressure values are then applied to a linear pulse contour model as described below. This second solution is more precise than the first solution.

On the basis of the Windkessel model, a mathematical equation can be written, which gives the relation between the arterial pressure signal, Pa(t) and the blood flow rate, q(t):

$$(1+Rao/Rp) \cdot q(t) + Rao \cdot Cw \cdot q'(t) = Pa(t)/Rp + Cw \cdot P'a(t) \quad (4)$$

wherein g'(t) and P'a(t) are the first-order derivatives in time of q(t) and Pa(t).

The value q(t) that is computed by means of this equation is in real time. The closing time of the heart valve can be accurately derived from the blood flow rate that has thus been computed by determining the time of the first local minimum after the beginning of the ejection phase of the heart. In order to arrive at an accurate computation of q(t), it is important that the correct value for Rao, Cw and Rp be known. The value of Rp can be computed from Rao and Cw by assuming that the total amount of blood that flows into the arterial vascular system during a heartbeat, or over a number of heartbeats, will also flow out of said arterial vascular system again. In other words, q(t)=0 is the value of q(t) to arrive at the end of a heartbeat.

According to a description by Murgo and Westerhof Girc Res (1984) 54: 666-673, the characteristic input resistance, Rao, is affected by the density of blood, ρ, CSA, and the specific arterial Windkessel compliance, C'w, as follows:

$$Rao = \sqrt{\frac{\rho}{(CSA \cdot C'w)}}$$

Figure 4:
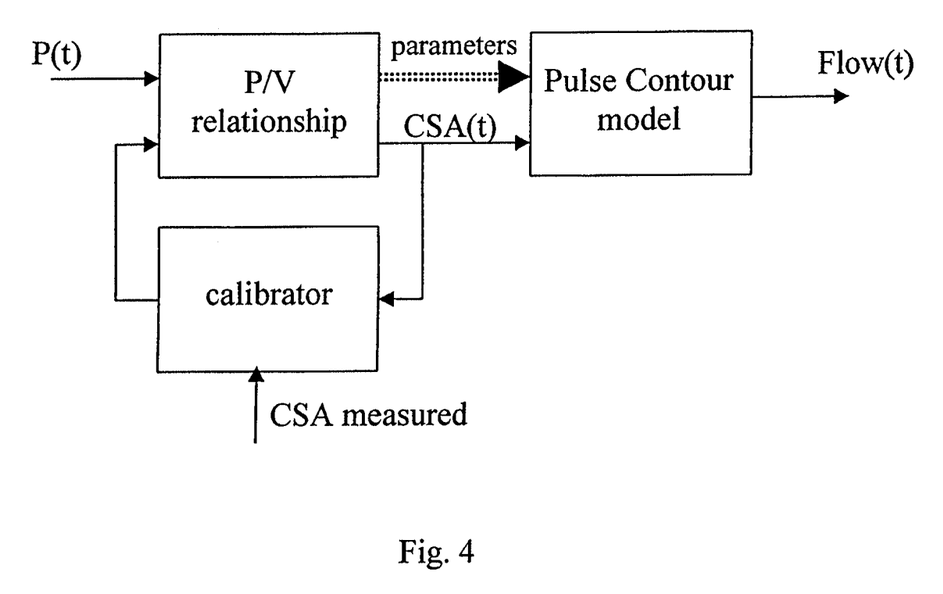
FIG. 4 schematically illustrates the correction of the pressure/CSA relationship, based on an independent measure of the CSA of the aorta and its application in a pulse contour model, for instance the model of FIG. 3.

C'w is the value of the first derivative of the patient-related pressure/CSA relationship at a measured pressure, Pa. The arterial Windkessel compliance (Cw) is given by multiplying C'w with an effective length of the arterial system, usually a length of 60 cm is chosen. Cw decreases substantially when aortic pressure increases. This non-linear behaviour of the aortic wall would be a major source of error if not taken into account in the manner as described above. To overcome the individual uncertainty in aortic CSA in each patient, a measurement of aortic diameter is carried out, for example with an ultra sound echo system (M-mode, HemoSonic 100, Arrow International Inc.). In this case, measured cross sectional area (CSA) is computed from the measured aortic diameter. The population-related pressure/CSA relationship is converted into a patient-dependent pressure/CSA relationship. Hereto, CSAmax of the arctangent relation between pressure and CSA is linearly scaled by multiplying CSAmax with the quotient CSA measured and CSA predicted by equation (1). This conversion as used in a pulse contour method is schematically shown in FIG. 4.

Figure 5:
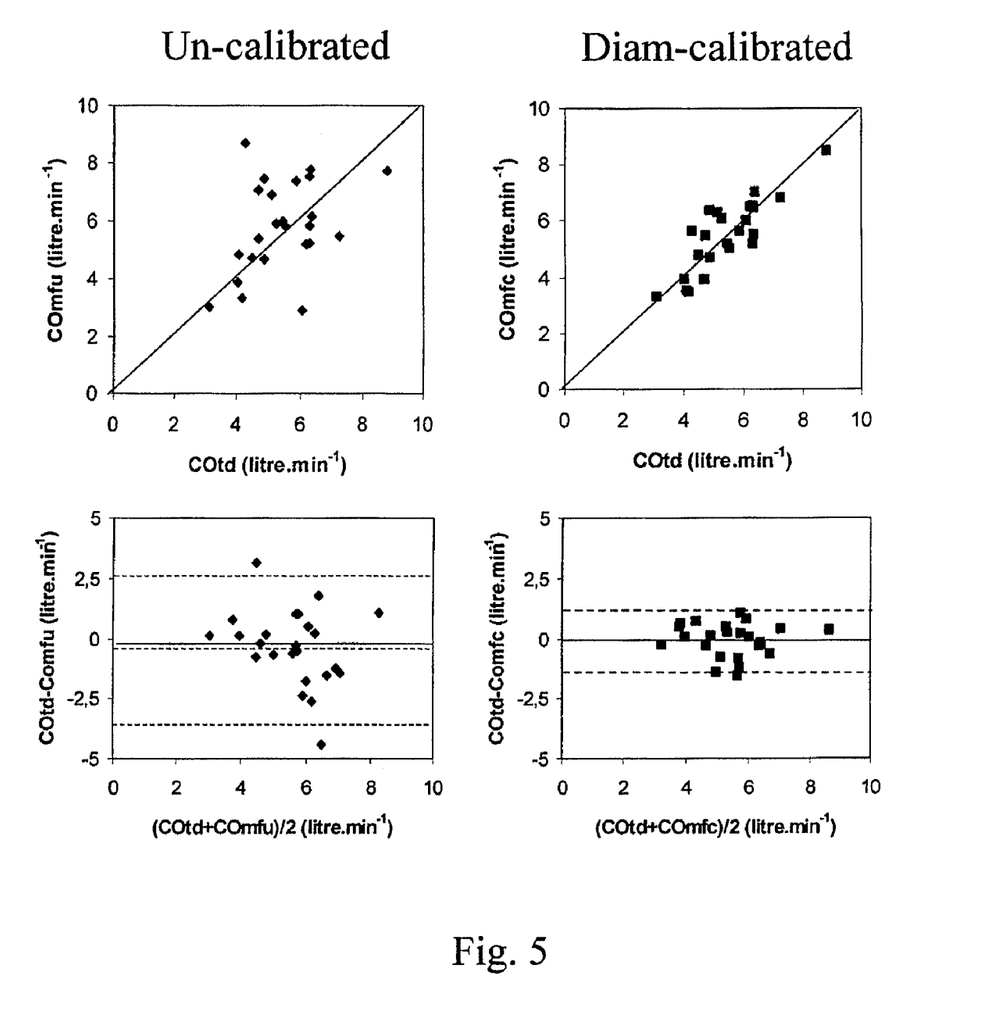
FIG. 5 is an example of the results of a pulse contour method based on a three element Windkessel model, which utilizes the arctangent relationship between pressure and CSA of the aorta.

The superior results of the patient-specific over the population based pulse contour approach are illustrated in a comparative study, see FIG. 5. This figure gives the data pairs of 24 patients before (left) and after (right) correction of the population-related to the individual patient-related pressure/CSA relationship. In the scatter diagrams, upper panels, the line of identity is given. The dashed lines in the Bland-Altman plots, lower panels, indicate bias (−7% and 1%) and limits of agreement (−62 to +50% and −27% to 24%) respectively.

Figure 6:
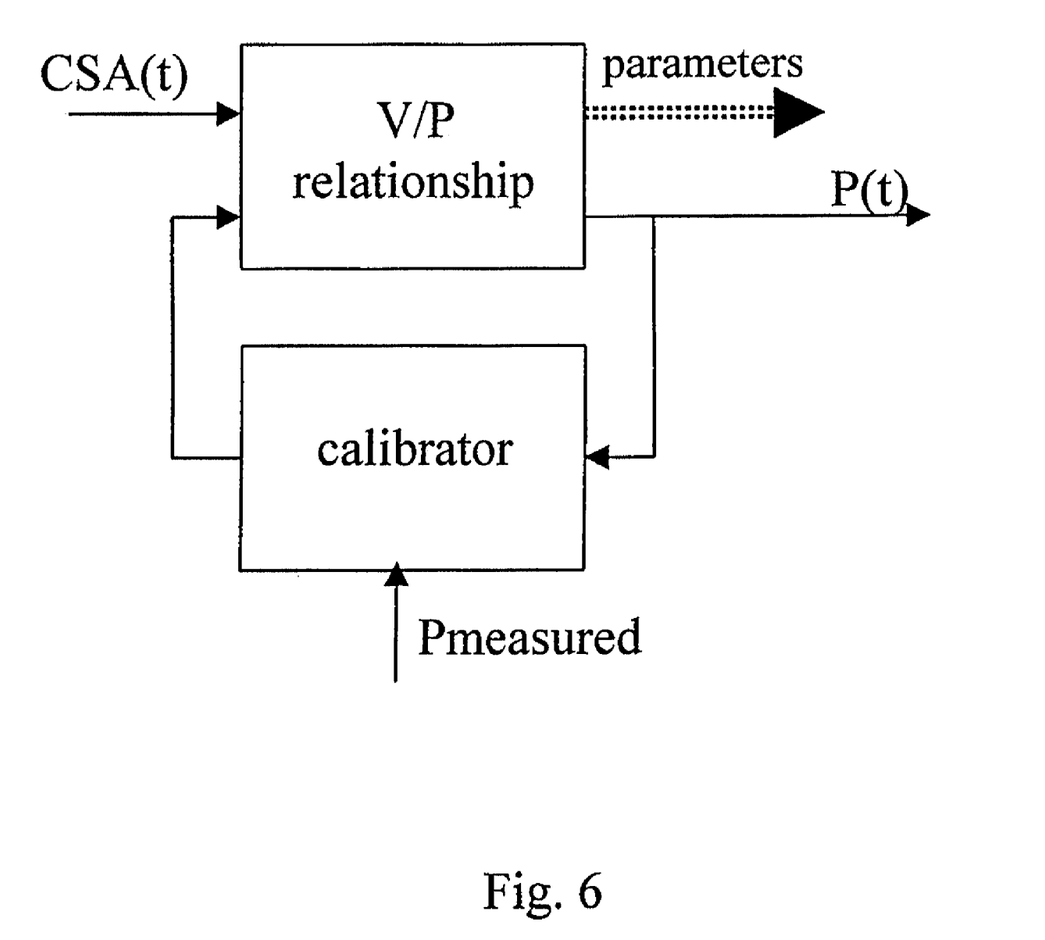
FIG. 6 schematically illustrates the prediction of the arterial pressure from a measure of the CSA of the aorta and the correction of the population related CSA/pressure relationship into a patient-related CSA/pressure relationship by means of an independent measure of the actual arterial pressure of a patient.

Further the invention provides a method to determine pressure from CSA measurements or CSA/pressure relationship. The determination of non-invasive continuous arterial pressure is done by using the volume or CSA/pressure relationship and is schematically illustrated in FIG. 6. Hereto, CSA of the aorta is determined, for instance with a transoesophageal ultra-sound system. For example by means of the following CSA/pressure relationship arterial pressure is calculated from the measured value of the CSA:

$$Pa = P0 + P1 * \tan\left[pi * \left(\frac{CSA}{CSA\max} - 0.5\right)\right] \quad (5)$$

where Pa is arterial pressure, P0, P1 and CSAmax are age, gender, length and weight related parameters of the tangent CSA/pressure relationship. These parameters are known from post mortem measurement on human aortas. Adaptation of this population-related CSA/pressure relationship to a patient-related CSA/pressure relationship is done by a single or multiple comparisons of the predicted pressure value with a measured pressure value. Hereto a measure of the arterial blood pressure is needed from, for example the non-invasive upper-arm Riva-Rocci-Korotkoff blood pressure measurement technique. This blood pressure measurement is next used to correct the volume/pressure relationship (see FIG. 6). Based on this principle, continuous monitoring of the arterial pressure can be obtained from a continuous measurement of the diameter or CSA of the aorta.

Figure 7:
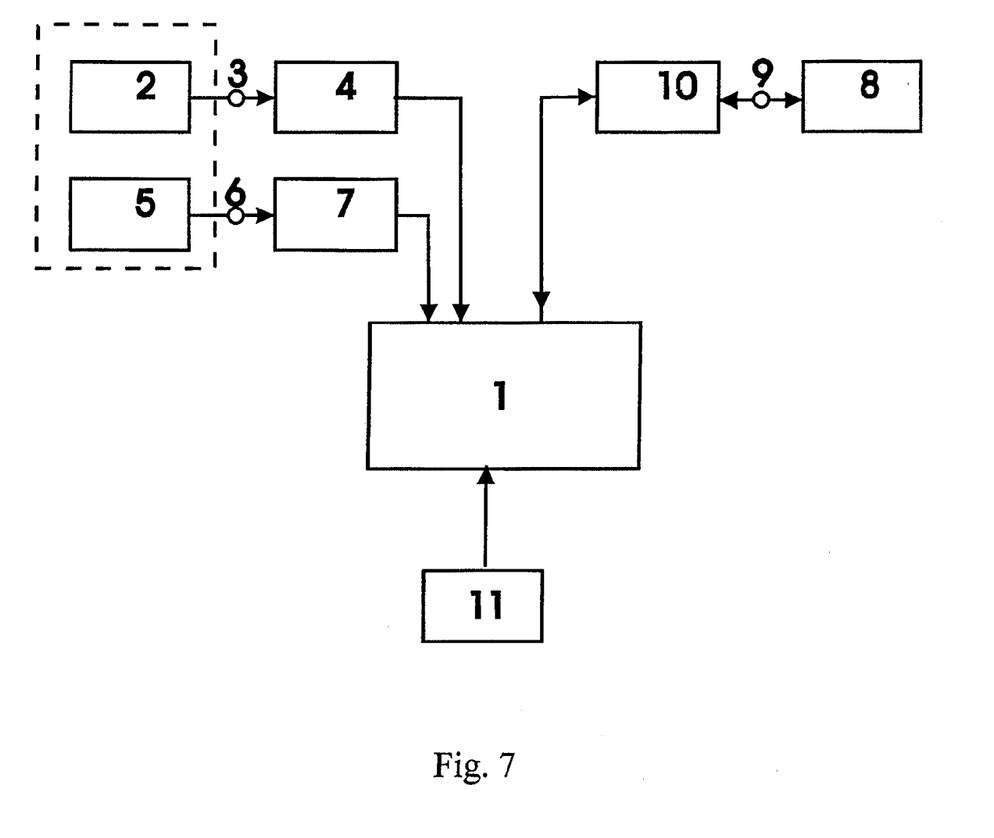
FIG. 7 is a block diagram showing a possible embodiment of an apparatus according to the invention.

FIG. 7 shows a strongly simplified block diagram of a possible embodiment of an apparatus of the invention. This embodiment comprises a processing unit 1, which includes an output element 10, by means of which for instance the estimated cardiac output or the estimated pressure can be outputted at 9 to another device 8. The device 8 might also be a display. The processing unit 1 has three inputs. Input 3 receives a blood pressure signal from a pressure sensor 2. The pressure signal is passed to the processing unit 1 via an amplifier 4. Input 6 receives a cross sectional area signal or diameter signal from an ultra-sound apparatus 5. This signal is passed to the processing unit 1 via amplifier 7. Further, an input 11 is provided for patient-related data, such as the patient's age, sex, weight and height, together with the mode of operation. Input 11 is also used to input mean arterial pressure in case no pressure sensor is connected or mean cross sectional area of the aorta or mean aortic diameter in case no ultra-sound device is connected.

The processing of the information depends on the mode of operation. In a mode according to FIG. 2, the patients age, sex, height, length are entered via input 11. An arterial pressure signal Pa(t) is applied to input 3. Using for example equation 1, 2 or 3, the processing unit 1 calculates based on data entered on input 11, the population-related pressure/volume (pressure/CSA) relationship. As soon as a CSA(t) signal is applied to input 6 or a mean value of CSA is entered via input 11, the population-related pressure/CSA relationship is converted or corrected to a patient-related pressure/CSA relationship. Next, from pressure Pa(t) the processing unit 1 computes a patient-related CSA(t) signal, which is outputted via the output 9.

In a mode according to FIG. 4, first, a patient-related pressure/CSA relationship is computed, in the same manner as in the mode according to FIG. 2. Second, for each pressure Pa($t_i$) the processing unit 1 computes from the patient-related pressure/CSA relationship the parameters of a Windkessel model. Third, the curve of the blood flow rate q(t) is computed from the blood pressure signal Pa(t), for example by means of the differential equation (4). Beat stroke volume delivered by the heart is found by integration of the blood flow over the systolic part of the heart beat. Cardiac output is found by multiplying stroke volume with heart rate. The cardiac output value can be shown on display device 8.

In a mode according to FIG. 6, the patients age, sex, height, length is entered via input 11. A signal of the cross sectional area of the aorta CSA(t) is applied to input 6. The processing unit 1 calculates based on this input via 11, the population-related CSA/pressure relationship. As soon as an arterial Pa(t) signal is applied to input 3 or a mean value of arterial Pa is entered via input 11, the population-related CSA/pressure relationship is corrected to a patient-related CSA/pressure relationship. Next, from pressure signal CSA(t) the processing unit 1 computes a patient-related Pa(t) signal, which is outputted via the output 9.

Other aspects of the invention include a computer program including a set of instructions capable, when incorporated in a machine-readable medium, of causing a system having information processing capabilities to implement the foregoing.

The invention is not restricted to the above described embodiments which can be varied in a number of ways within the scope of the claims.

The invention claimed is:

1. A method for determining at least one patient-related parameter for monitoring a patient, comprising:
   using a general population-related non-linear relationship between pressure and cross-sectional area (CSA) of an arterial vascular bed and information indicative of the arterial pressure of the patient to obtain a prediction of the cross sectional area (CSA) of the thoracic part of the aorta of the patient; and
   using a processor to correct at least one parameter of the general population-related relationship using information indicative of a measured cross sectional area of the thoracic part of the aorta of the patient to determine a patient-related non-linear relationship between pressure and cross sectional area (CSA) such that the cross sectional area obtained with the patient-related relationship is equal to the measured cross sectional area.

2. The method according to claim 1, and further comprising comparing the predicted value of CSA to the measured CSA value to obtain a calibration value, wherein the calibration value is used to linearly scale the CSA values obtained by the general population-related non-linear relationship.

3. The method according to claim 1, wherein the information of the measured CSA is obtained from a measure of the diameter of the aorta.

4. The method according to claim 1, wherein a three element windkessel pulse contour model is used to determine patient-related parameter(s) including at least one of blood flow, stroke volume or cardiac output, wherein a characteristic input resistance, Rao, and an arterial compliance, Cw, of the three element windkessel pulse contour model are derived from the patient-related relationship.

5. The method according to claim 4, wherein a third parameter of the three element windkessel pulse contour model is obtained based on criteria that blood flow just before start of the ejection-phase of a heart is zero.

6. The method according to claim 4, wherein the patient-related relationship is used to calculate volume changes of an arterial system.

7. The method according to claim 6, wherein the patient-related relationship is used to transform the arterial pressure, which next is used is an output to a linear differential equation which has as an output the blood flow.

8. The method according to claim 7, wherein the blood flow is integrated over the systolic phase of a heartbeat to derive stroke volume of the heart.

9. A method for determining at least one patient-related parameter for monitoring a patient, comprising:
   using a general population-related non-linear relationship between cross sectional area (CSA) and pressure of an arterial vascular bed and information indicative of measuring a cross sectional area (CSA) of a thoracic part of an aorta of the patient to obtain a prediction of arterial pressure; and
   using a processing unit to correct at least on parameter of the general population-related non-linear relationship between cross sectional area (CSA) and pressure using information indicative of a measured arterial pressure to determine a patient-related non-linear relationship between cross sectional area (CSA) and pressure, wherein the arterial pressure obtained with the patient-related relationship is equal to the measured arterial pressure.

10. The method according to claim 9, and further comprising comparing the predicted value of the arterial pressure to the measured pressure value to obtain a calibration value, wherein the calibration value is used to linearly scale pressure values obtained by the general population-related non-linear relationship.

11. The method according to claim 9, wherein the information of the measured CSA is obtained from a measure of a diameter of the aorta.

12. An apparatus for monitoring a patient comprising:
a processing unit configured to receive information indicative of an arterial pressure of a patient and a general population-related non-linear relationship between pressure and cross sectional area (CSA) of an arterial vascular bed and to calculate a prediction of a cross sectional area (CSA) of a thoracic part of an aorta of the patient, the processing unit further configured to receive information indicative of a measurement of a cross sectional area of the thoracic part of the aorta and to correct at least one parameter of the general population-related non-linear relationship using the measured cross sectional area to determine a patient-related non-linear relationship between pressure and cross sectional area (CSA) such that the cross sectional area obtained with the patient-related relationship is equal to the measured cross sectional area.

13. A non-transitory computer readable medium comprising a computer program including a set of instructions, which, when executed on a computer, causes the computer to implement a method for determining at least one patient-related parameter for monitoring a patient, comprising:
using a general population-related non-linear relationship between pressure and cross sectional area (CSA) of an arterial vascular bed and information indicative of arterial pressure of the patient to obtain a prediction of cross sectional area (CSA) of a thoracic part of an aorta of the patient; and
correcting at least one parameter of the general population-related non-linear relationship using information indicative of a measured cross sectional area of the thoracic part of the aorta of the patient to determine a patient-related non-linear relationship between pressure and cross sectional area (CSA) such that the cross sectional area obtained with the patient-related relationship is equal to the measured cross sectional area.

14. An apparatus for monitoring a patient comprising:
a processing unit configured to receive information indicative of measuring a cross sectional area (CSA) of a thoracic part of an aorta of a patient and a general population-related non-linear relationship between pressure and cross sectional area (CSA) of an arterial vascular bed and to calculate a prediction of an arterial pressure, the processing unit further configured to receive information indicative of a measurement of arterial pressure and to correct at least one parameter of the general population-related non-linear relationship using the measured cross sectional area to determine a patient-related non-linear relationship between cross sectional area (CSA) and pressure, wherein the arterial pressure obtained with the patient-related relationship is equal to the measured arterial pressure.

15. A non-transitory computer readable medium comprising a computer program including a set of instructions, which, when executed on a computer, causes the computer to implement a method for determining at least one patient-related parameter for monitoring a patient, comprising:
using a general population-related non-linear relationship between cross sectional area (CSA) and pressure of an arterial vascular bed and information indicative of measuring a cross sectional area (CSA) of a thoracic part of an aorta of the patient to obtain a prediction of arterial pressure; and
correcting at least one parameter of the general population-related non-linear relationship using information indicative of a measured arterial pressure to determine a patient-related non-linear relationship between cross sectional area (CSA) and pressure, wherein the arterial pressure obtained with the patient-related relationship is equal to the measured arterial pressure.

* * * * *